United States Patent [19]

Engstrom

[11] 4,205,677
[45] Jun. 3, 1980

[54] CARDIOTOMY SUCTION CONTROL SYSTEM AND VALVE

[76] Inventor: William R. Engstrom, 17 Willow St., Belmont, Mass. 02178

[21] Appl. No.: 881,404

[22] Filed: Feb. 27, 1978

[51] Int. Cl.² ............................................. A61M 1/00
[52] U.S. Cl. .................................... 128/276; 128/274; 32/33; 433/95
[58] Field of Search ............... 128/214 R, 214 F, 227, 128/DIG. 3, 274, 276; 137/597; 15/409, 330; 251/25; 32/33

[56] References Cited

U.S. PATENT DOCUMENTS

| | | | |
|---|---|---|---|
| 2,597,966 | 5/1952 | Adler | 128/276 |
| 3,071,402 | 1/1963 | Lasto et al. | 128/276 UX |
| 3,516,405 | 6/1970 | Hopper | 15/330 |
| 3,525,118 | 8/1970 | Viollet | 15/330 |
| 3,595,234 | 7/1971 | Jackson | 128/276 |
| 3,610,242 | 10/1971 | Sheridan et al. | 128/276 |

Primary Examiner—Robert W. Michell
Assistant Examiner—J. Kruter
Attorney, Agent, or Firm—Morse, Altman, Oates & Bello

[57] ABSTRACT

A suction control system is provided for use by surgeons in recovering blood from a patient during the course of a surgical operation. A blood suction line extends from a pick-up tube, which is placed in the blood pool of the patient, to a cardiotomy reservoir. Attached to the blood suction line, but not communicating with it, is a vernier control valve to which two vacuum lines are connected and which valve is formed with a port and connecting passage between the two vacuum lines. One vacuum line is connected to a vacuum source while the other vacuum line connects to the cardiotomy reservoir. The valve is formed with an internal passage connecting the two vacuum lines and a port open to the atmosphere and communicating with the passage. The surgeon holds the valve unit in his hand with his thumb over the port. By moving his thumb back and forth he is able to control from zero to maximum the level of vacuum at the reservoir and thereby control the rate at which the blood is drawn through the blood suction line from the patient or stop the flow entirely.

3 Claims, 7 Drawing Figures

CARDIOTOMY SUCTION CONTROL SYSTEM AND VALVE

BACKGROUND OF THE INVENTION

1. Field of the Invention

This invention relates generally to blood control systems for use by surgeons and more particularly is directed towards a new and improved cardiotomy suction circuit.

2. Description of the Prior Art

In many surgical procedures and particularly in open heart surgery, a serious problem has existed in controlling the rate at which blood is sucked from the area in and around that portion of the patient being operated upon. In practice, a relatively large pool of blood will form in a body cavity and this blood normally is returned to the patient through auto-transfusion, after first being oxygenated. Systems presently available for collecting blood in this manner are commonly referred to as cardiotomy suction circuits, and those currently in use involve direct suction lines, with the suction rate being controlled by various techniques such as foot pedals, finger-operated open ports on the suction line, remote control switches for pumps and other means. None of the systems heretofore available has been entirely satisfactory for various reasons. For example, the foot operated pedals may be accidentally displaced by members of the operating team kicking the pedal, which is then hard to find under the operating table. The use of an open port on a direct blood suction line subjects the blood to continuous negative pressure as well as exposing the blood to the rushing, incoming air. The continuous negative pressure applied to the blood is harmful to the blood cells and the frothing action produced in the blood by the continuous air flow in the blood is a major source of hemolysis. Also, any bacterial contamination of the operating room air may produce direct inoculation into the patient's blood since more than 2000 liters of room air may be bubbled into the patient's blood during a typical two hour pump run. Other systems have been developed but also have been found unsatisfactory from the standpoint of efficiency, simplicity, control and blood protection.

Accordingly, it is an object of the present invention to provide a new and improved cardiotomy suction control system. Another object of this invention is to provide a vernier suction control system for use in surgical operations whereby blood collected by a suction system is transferred in a substantially closed system without being exposed to continuous negative pressure or to ambient air.

SUMMARY OF THE INVENTION

This invention features a system for suctioning blood from a pool which collects in the body cavity of the patient during the course of various surgical operations, comprising a valve block formed with an internal cross-over passage and an open port, which block is held by the surgeon so that the port may be opened and closed by the surgeon's thumb or finger. A first blood conduit is connected at one end to a cardiotomy reservoir and at the other end is provided with a suction tip for placement in the blood pool. A second conduit is connected at one end to the cardiotomy reservoir and at the other end to the valve block in communication with the cross-over passage. A third conduit is connected at one end to the valve block and to the cross-over passage, and at the other end to a continuous suction source. When the port is closed or partially closed, a vacuum from the third line will create a vacuum in the second line to produce a temporary negative pressure in the reservoir, causing blood to be drawn from the blood pool through the blood suction line to the reservoir. When the port is open, the vacuum is broken, stopping the blood flow, with intermediate vacuum levels and flow rates created by the position of the surgeon's thumb over the port.

DETAILED DESCRIPTION OF THE PREFERRED EMBODIMENT

Figure 1:
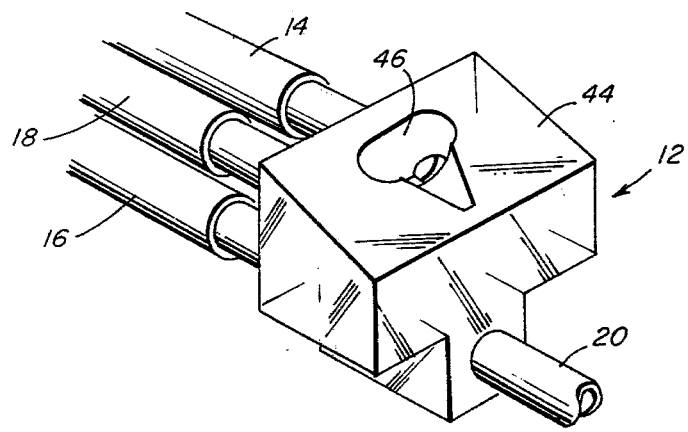
FIG. 1 is a view in perspective of a valve connecting head made according to the invention and forming part of the system.
Figure 2:
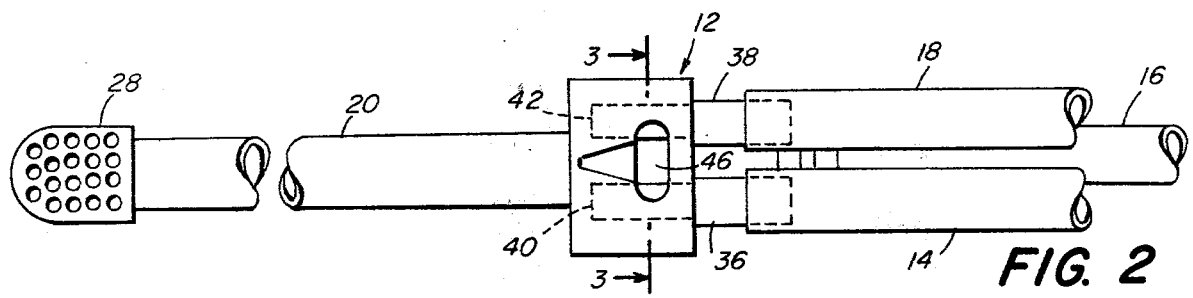
FIG. 2 is a top plan view thereof.
Figure 3:
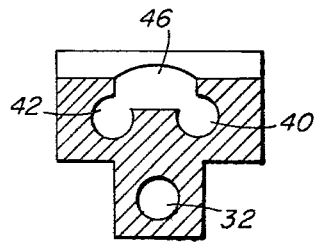
FIG. 3 is a cross-sectional view taken along the line 3—3 of FIG. 2.

Referring now to the drawings, the reference character 10 generally indicates a suction system primarily for use by surgeons during the course of performance of surgical operations, especially open heart surgery where a substantial amount of blood collects in the body cavity within the area being operated upon. In such operations, it is desirable to auto-transfuse the patient and minimize the necessity of homologous transfusion of blood.

The system 10 is generally organized about a vernier valve block 12 to which are connected flexible tubular conduits 14, 16 and 18 and a flexible pick-up tube 20. The conduit 18 is connected through a vacuum regulator 22 to a vacuum source, such as a vacuum pump, wall vacuum connection, or the like. The conduit 14 connects the valve block 12 to the upper end of a cardiotomy reservoir 24 in which blood collected by the system is stored and subsequently returned to the patient normally through an oxygenator (not shown) connected to the reservoir by means of a tube 26. The blood conduit 16 is connected to the lower end of the reservoir 24 and is attached to the valve block 12 in direct communication with the pick-up tube 20. The pick-up tube 20 may be formed integrally with the valve unit 12 or may be detachably connected thereto. The free end of the tube 20 normally is provided with a strainer tip 28 which is placed in the blood pool that normally forms in a cavity of the patient during the course of an operation such as open heart surgery. The suction tip may be provided in a variety of lengths and typically is on the order of perhaps 9" to a foot or so, as desired.

The tubings 14, 16 and 18 typically are provided in 10' lengths and, in practice, it has been found that ¼" inside diameter tubing with a 1/16" wall thickness functions satisfactorily. Preferably, the tubing is of a clear, flexible plastic material.

The valve block 12, in the illustrated embodiment, is a one-piece unit of a relatively rigid material and typically the material may be clear, hard acrylic plastic, although other materials may be employed to advantage. In any event, the block 12, which is relatively small, typically 1¼" wide ×1¼" high and approximately ¾" deep, includes the pick-up tube 20 which is formed integral with the block and extends from the forward lower face thereof. Extending coaxially with the tube 20 from the rear face of the block is an integral tubular connector 30 which communicates with the pick-up tube 20 through an internal passage 32 formed through the lower portion of the block. The connector 30 may be formed with serrations 34 in order to provide a tight fit with the tube 16 which is pressed over the end of the connector. Extending from the rear face of the upper portion of the block is a pair of tubular connectors 36 and 38 integral with the block and adapted to receive the ends of the tubes 14 and 18 which are pressed thereon. The connectors 36 and 38 may also be serrated to insure a tight grip with the tube ends.

Figure 4:
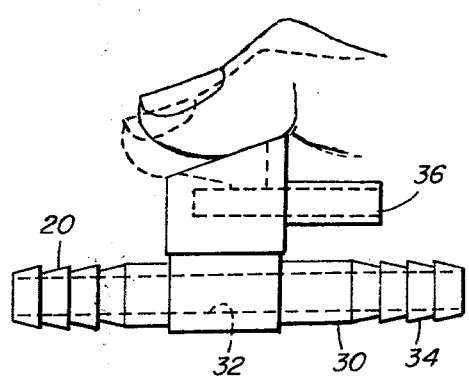
FIG. 4 is a detailed view in side elevation demonstrating the operation of the valve head.
Figure 5:
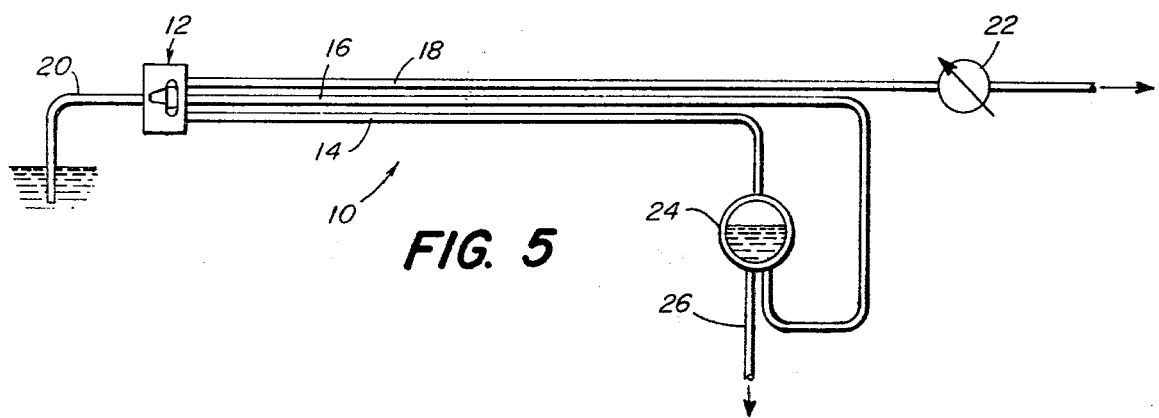
FIG. 5 is a schematic diagram of the system.

The block is formed with a pair of internal longitudinal passages 40 and 42 which communicate with the connectors 36 and 38 and extend lengthwise of the block. The block 12 is formed with an upper face 44 which preferably is inclined forwardly and downwardly and is formed with a port 46 in the center portion thereof. The port 46 extends downwardly into the block forming a transverse connecting passage between the longitudinal passages 40 and 42. The port 46 is somewhat triangular and extends in a narrowing slot towards the front face of the block. At its widest point, the port 46 typically is about ½" wide so that the port may be fully closed by a surgeon placing his thumb entirely over the port, as suggested in FIG. 4. The surgeon may rock or slide his thumb back and forth across the inclined face 44 of the block so as to fully close, fully open, or partially open the port. Depending upon the position of the surgeon's thumb, a wide variety of effective port sizes can be produced to accurately control the flow of blood through the system.

The system operates by placing the pick-up tube with the tip 28 in the pool of blood and connecting the line 18 to a vacuum source. With the other two lines 14 and 16 connected to the blood reservoir 24 in the manner illustrated, the surgeon can quickly and easily control the flow of blood from the tube 20 through the line 18 into the reservoir. With the port 46 fully opened, the vacuum in the line 18 is broken and no vacuum will be created in the line 14 and no blood will flow. However, if the surgeon closes or partially closes the port, vacuum will be created immediately in the line 14, building up a negative pressure within the reservoir 24. This negative pressure will thus cause blood to flow through the line 16 and through the pick-up tube 40, with the rate of flow being controlled by the position of the surgeon's thumb over the port.

The thumb actuated valve thus regulates the pressure in the cardiotomy reservoir so that negative pressure is present only when the valve is fully or partially closed during actual suctioning of blood. When the valve is opened by release of the thumb, pressure in the reservoir becomes atmospheric. Thus, no continuous air is sucked through this circuit when it is not in use. Since the system minimizes the negative pressure on the blood and substantially reduces exposure of the blood to ambient air, as well as eliminating frothing, very little hemolysis is produced. Also, the substantially closed system greatly reduces the bacteria level picked up by the blood during the auto-transfusion process.

Figure 6:
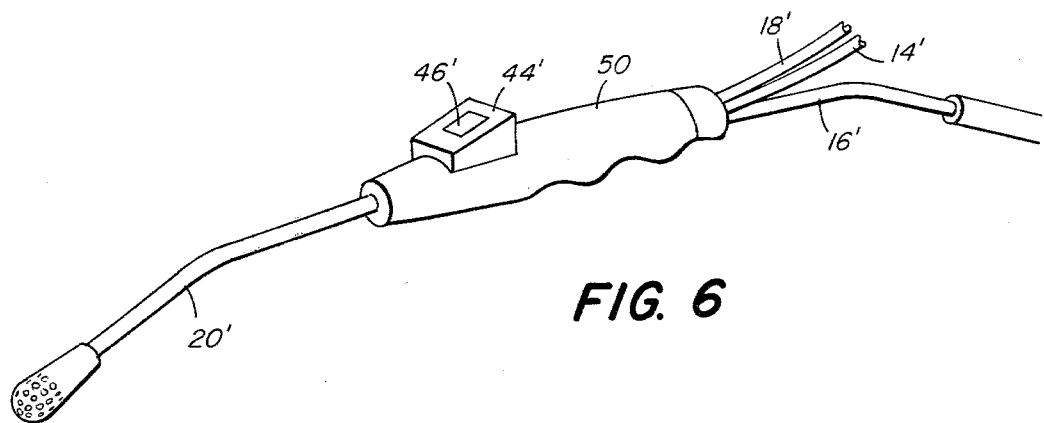
FIG. 6 is a perspective view showing a modification of the invention, and, FIG. 7 is a perspective view, somewhat schematic, showing another modification of the invention.

Referring now to FIG. 6, there is illustrated a modification of the invention and in this embodiment a valve block 12', together with an associated pick-up tube 20', bloodline 16', and vacuum lines 14' and 18' are incorporated with an integrated handle 50 providing a convenient and easily manipulated instrument. The handle 50 is of a length sufficient to be gripped by the hand and may be molded from plastic or other suitable material. The block 12' is positioned at the forward end of the handle on its upper side and includes an inclined face 44' through which a port 46' is provided as in the principal embodiment. The handle is formed with internal passages connecting appropriately to the vacuum lines and the bloodlines, the bloodlines being kept separate from the vacuum lines, as in the principal embodiment. The pick-up tube 20' preferably is of a rigid tubular material, such as aluminum or, if preferred, may be of a transparent plastic, allowing the physician to visually verify blood flow through the tube. The instrument is used in the same manner as that shown in the principal embodiment with vacuum being controlled by placement of the thumb over the port 46'.

Figure 7:
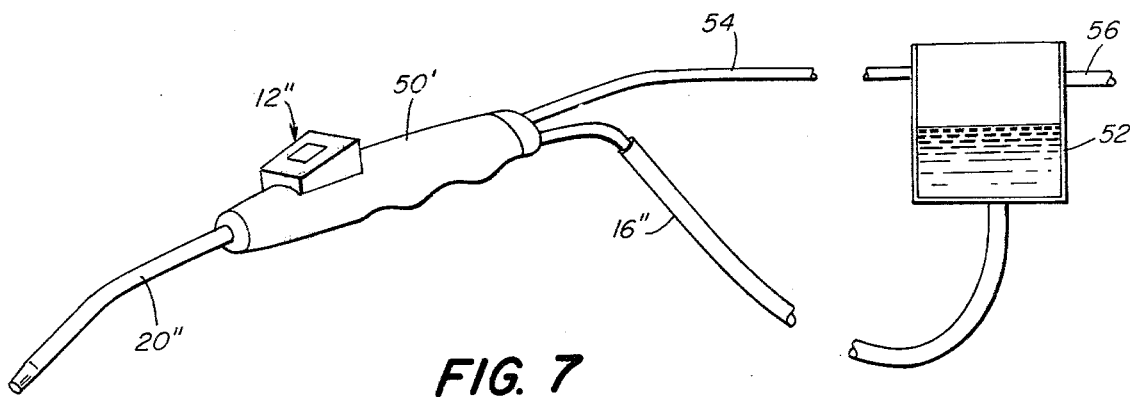

Referring now to FIG. 7 of the drawings, there is illustrated a further modification of the invention and in this embodiment a handle 50', similar to that of the FIG. 6 embodiment, includes a rigid pick-up tube 20" communicating with a blood conduit 16" connecting to a reservoir 52. However, in this embodiment a single vacuum line 54 is provided and is connected between the upper portion of the reservoir 52 and a block 12", with the level of vacuum being controlled by the operator's thumb over the block port, as before. The reservoir 52 is connected by a conduit 56 to a vacuum source with blood flow being controlled by the operator opening and closing the port in the block 12'.

Having thus described the invention what I claim and desire to obtain by Letters Patent of the United States is:

1. A surgical suction system for withdrawing from an animal patient blood or the like, comprising
   (a) a closed chamber adapted to store a quantity of blood,
   (b) a first tubular conduit connected at one end to a lower portion of said chamber and in communication with the interior, the other end of said conduit adapted to be immersed in a source of said patient's blood,
   (c) a valve having a body connected to said first conduit and formed with a pair of passages and a port interconnecting both of said passages and normally open to the atmosphere,
   (d) a second tubular conduit separate from said first conduit and connected to one of said passages and to a vacuum source, and,
   (e) a third tubular conduit separate from said first conduit and connected to the other of said passages and to an upper portion of said chamber whereby the vacuum in said third conduit and said chamber, and the flow of blood through said first conduit may be selectively controlled by manually opening and closing said port.

2. A suction system, according to claim 1, wherein said port is open through one face of said valve and is of a generally triangular outline.

3. A suction system, according to claim 1, wherein said valve includes a third passage separate from said pair of passages and communicating with said first conduit and a pick-up tube connected to said valve and communicating with said third passage.

* * * * *